(12) United States Patent
Asher et al.

(10) Patent No.: US 6,881,381 B1
(45) Date of Patent: Apr. 19, 2005

(54) APPARATUS FOR MARKING AND IDENTIFYING LIQUIDS

(75) Inventors: William E. Asher, Leominister, MA (US); Richard H. Clarke, Boston, MA (US); Mohammad S. Farahat, Westboro, MA (US)

(73) Assignee: On-Site Analysis, Inc., Marlborough, MA (US)

( * ) Notice: Subject to any disclaimer, the term of this patent is extended or adjusted under 35 U.S.C. 154(b) by 0 days.

(21) Appl. No.: 09/219,288

(22) Filed: Dec. 22, 1998

Related U.S. Application Data

(63) Continuation-in-part of application No. 08/885,164, filed on Jun. 30, 1997, now Pat. No. 5,958,780.

(51) Int. Cl.$^7$ .............................................. G01N 33/26
(52) U.S. Cl. ..................... 422/68.1; 422/82.05; 250/343; 250/339.09; 250/339.11; 250/339.12; 73/61.43; 73/61.44; 436/56; 436/60
(58) Field of Search ............................. 436/52, 69, 27, 436/161, 106, 139; 73/61.43, 61.44; 250/303, 343, 339.09, 339.11, 339.12; 422/50, 82.05, 68.1

(56) References Cited

U.S. PATENT DOCUMENTS

| | | | |
|---|---|---|---|
| 4,209,302 A | 6/1980 | Orelup | 44/59 |
| 4,278,444 A | 7/1981 | Beyer et al. | 44/59 |
| 4,606,859 A | 8/1986 | Duggan et al. | 540/122 |
| 4,918,020 A | 4/1990 | Nowak | 436/56 |
| 5,139,334 A * | 8/1992 | Clarke | 356/301 |
| 5,156,653 A | 10/1992 | Friswell et al. | 44/328 |
| 5,225,679 A | 7/1993 | Clarke et al. | 250/343 |
| 5,229,298 A | 7/1993 | Zoumalan | 436/111 |
| 5,279,967 A | 1/1994 | Bode | 436/56 |
| 5,466,826 A | 11/1995 | Cuthbert | 548/511 |
| 5,474,937 A | 12/1995 | Anderson et al. | 436/56 |
| 5,525,516 A | 6/1996 | Krutak et al. | 436/56 |
| 5,569,922 A | 10/1996 | Clarke | 250/339.12 |
| 5,677,186 A | 10/1997 | Anderson et al. | 436/56 |
| 5,677,187 A | 10/1997 | Anderson et al. | 436/56 |
| 5,742,064 A * | 4/1998 | Infante | 250/458.1 |
| 5,792,610 A * | 8/1998 | Witney et al. | 436/6 |
| 5,862,512 A * | 1/1999 | Voorhees et al. | 702/2 |
| 6,025,200 A * | 2/2000 | Kaish et al. | 436/56 |
| 6,274,381 B1 * | 8/2001 | Pauls et al. | 436/56 |

FOREIGN PATENT DOCUMENTS

| | | |
|---|---|---|
| AU | B-45678/93 | 2/1994 |
| EP | 0327163 | 8/1989 |
| EP | 0512404 | 11/1992 |
| WO | 9412874 | 6/1994 |
| WO | WO 95/06249 | 3/1995 |

OTHER PUBLICATIONS

Coulombe, "Chemical Markers in Weathered Gasolines," J.of Forensic Sciences, vol. 40, No. 5, Sep. 1995, pp. 867–873.*

Coulombe, R., "Chemical Markers in Weathered Gasoline", Journal of Forensic Sciences, JFSCA, vol. 40, No. 5, (Sep. 1995) pp. 867–872.

* cited by examiner

Primary Examiner—Lyle A. Alexander
(74) Attorney, Agent, or Firm—Thomas J. Engellenner; Kevin M. Cronin; Nutter McClennen & Fish LLP

(57) ABSTRACT

A liquid can be marked for identification purposes with at least first and second miscible markers. The markers are mixed in the liquid so that the ratio of the concentration of the first marker to the concentration of the second marker is substantially equal to a predetermined value. Thus, by comparing the ratio of the measured concentration of the first marker to the measured concentration of the second marker with predetermined values the liquid can be uniquely identified. The detectors can be connected to a processor and control unit (22) for initiation of testing, for processing of detection signal from the detectors, and for display of readout information. Processor and control unit (22) can include a look up table (23) for storing information about marking patterns, a comparison element (35) for comparing measured values with values supplied by look up table (23), and a display (30).

24 Claims, 10 Drawing Sheets

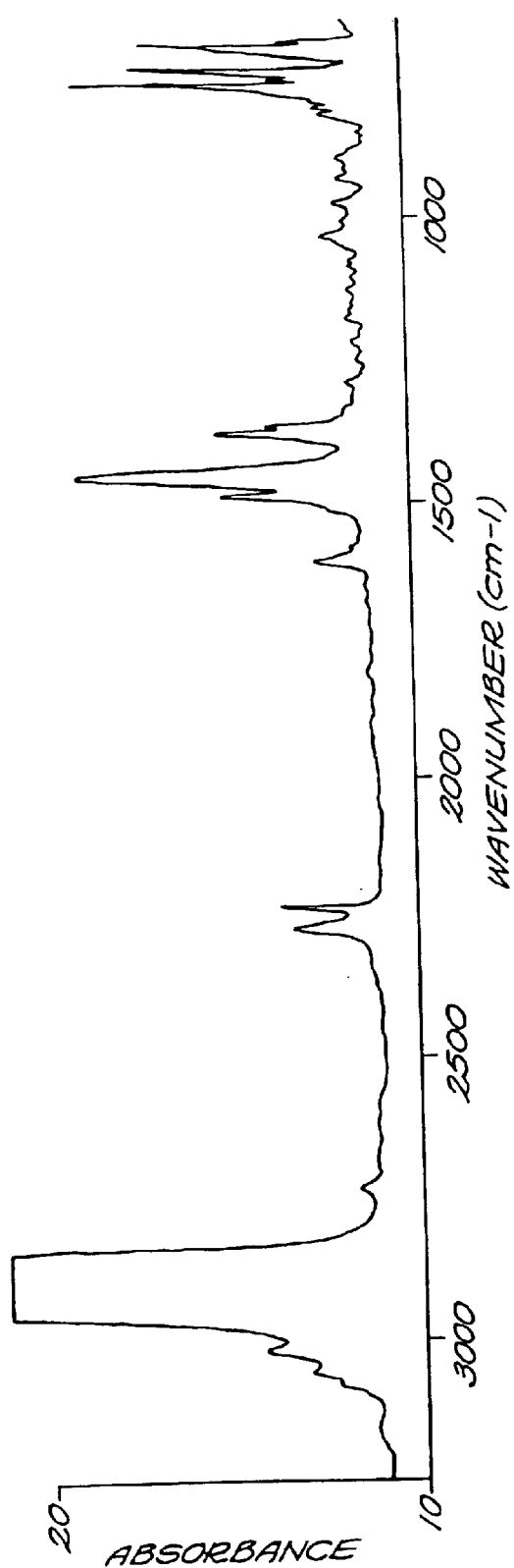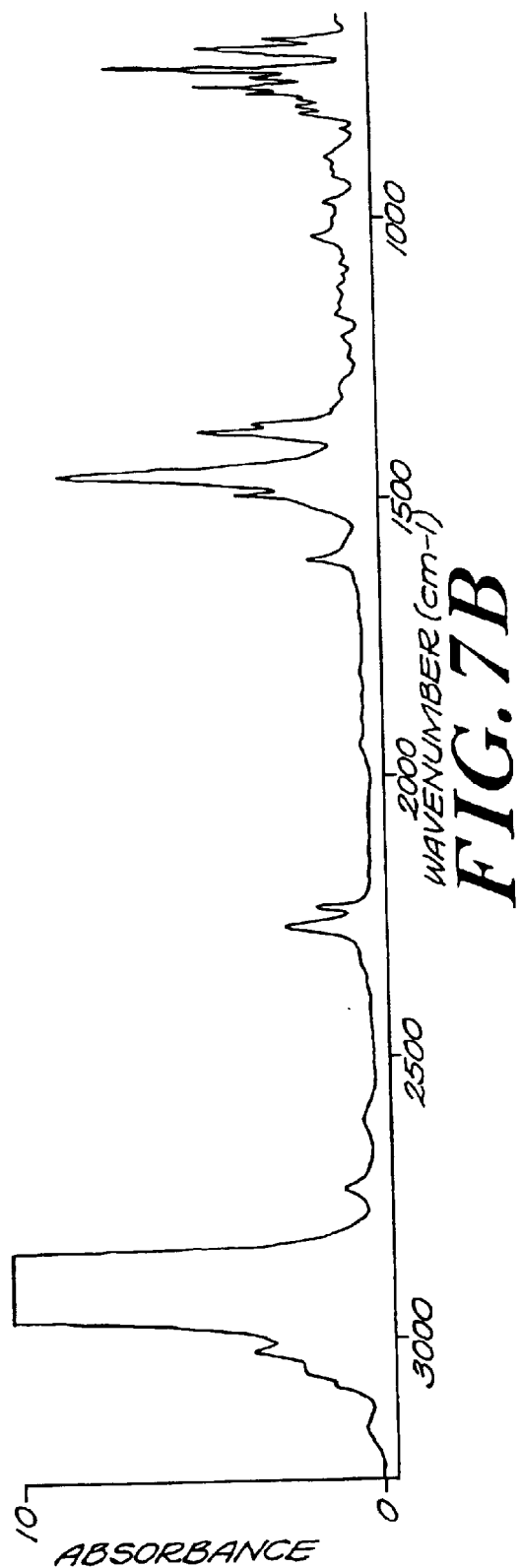

APPARATUS FOR MARKING AND IDENTIFYING LIQUIDS

REFERENCE TO RELATED APPLICATION

This application is a continuation-in-part of U.S. patent application Ser. No. 08/885,164, filed Jun. 30, 1997 now U.S. Pat. No. 5,958,780.

BACKGROUND OF THE INVENTION

The present invention is related to liquid identification. In particular, the present invention involves methods for marking a liquid and methods and systems for the identification of a liquid using at least one chemical marker.

There is a need for novel markers which are suitable for marking liquids such as petroleum fuels. There is also a need for methods of marking, tagging, or otherwise identifying liquids, and methods for distinguishing such marked liquids from otherwise identical but unmarked liquids.

These needs arise primarily from differing price or tax structures of different fuels or even the same fuel used for different purposes. For example, gasoline used for off-highway, non-vehicular purposes such as mining, lumbering or fishing, is commonly taxed at lower rates than that for highway vehicular use. Further, certain grades of oil are used interchangeably for heating oil or for diesel motor fuel. These situations can lead to abuse of the tax laws and cheating by unscrupulous persons.

It is, of course, necessary that the added chemical marker be capable of quick and relatively simple identification by non-scientific personnel. In other instances and aside from tax matters, there are occasions when it is desirable to mark a particular production batch of fuel or solvent to prove the origin of the material. As is readily apparent, any marker so used must be added in small concentration, should not affect the physical or chemical properties of the substances to which it is added and should be easily identified by relatively quick and simple means.

It is desirable to have simple, rapid and sensitive methods to detect the presence of one petroleum product in another. Fuels are sometimes mixed for the purpose of adulterating a higher priced product with a lower priced material, such as the addition of regular grade gasoline to premium gasoline, or for the purpose of evading taxation by the addition of low-taxed light heating oil to highly taxed diesel fuel. Other reasons for identifying particular fuels are determination of theft, or locating leaks from storage facilities at service stations, oil terminals, large scale industrial lubrication systems, or automotive transmission and hydraulic systems.

Thus, chemical markers are often added to a petroleum product to identify the product for a variety of reasons. Markers are used to differentiate among various grades of fuel. For example, markers are used to distinguish premium from regular grade gasolines, or aviation gasoline from motor gasoline. Markers are also widely employed to identify proprietary or specific brands of fuel from a particular refiner. Further, markers are sometimes required by government regulation to monitor the tax classification of diesel fuel, home heating oil, and kerosenes; in the case of tax classification monitoring, markers are used for the identification of petroleum products that might be substituted illegally for more costly or higher taxed fuels.

Most fuel markers are characterized by several important chemical properties. They are miscible in fuel, difficult to remove from the product by any simple treatment (e.g. filtering, bleaching, reactive conversion in the fuel), easily identifiable and, in some cases, quantifiable by the user. Further, for both cost and fuel performance reasons, markers are usually deployed in low concentrations, e.g., in the parts per million (volume/volume) range, and must be effective in their role as product identifiers at such low concentrations.

Markers are often organic dyes, materials with strong absorbency in the visible portion of the electromagnetic spectrum. Thus, a fuel containing such organic dyes immediately provides information to an observer. The red dye, Red-26, is an example of such a marker. Red-26 is used by the IRS to distinguish nontaxed home heating oil in the US from other taxed fuels of similar composition. If red dye is present, no federal taxes have been paid on the product. Presence of red color in the product is taken as evidence of tax evasion if the fuel is sold as taxed commercial diesel.

In many cases, however, it is desirable that the marker material not be visible in the product. Markers that are not visibly discernible are termed "silent markers." Silent markers identify a product to an authorized tester. However, silent markers do not provide any visual indication of the identity of the product to the regular or non-authorized user. Silent markers must also be miscible with the fuel and should be difficult to remove (e.g., by ultrafiltration). Similarly, silent markers must be detectable by a subsequent manipulation of a sample from the product.

In order to detect the presence of a silent marker, many of the existing markers must be extracted by a chemical process. Typically, the chemical process includes shaking a sample of the product with a water-based reagent. The addition of a chemical agent to the water phase causes the extract to turn to a visibly distinct color. The depth of the color indicates the quantity of marker present in the sample. A laboratory measurement in a spectrometer indicates the concentration of marker present in the isolated sample. Comparing the measured concentration with the original concentration of marker in the fuel assists in the identification of the fuel.

In contrast, some silent markers are large organic molecules that either absorb or fluoresce in the near infrared to mark their presence in a fuel sample. U.S. Pat. No. 5,525,516 (Eastman Chemical), incorporated herein by reference, and German Patent DE4224301A1 (BASF) describe such markers. In U.S. Pat. No. 5,525,516, the presence of such a silent marker is detected by exposing the marker to near infrared radiation and then detecting emitted fluorescent light via a near infrared light detection element. However, there are only a finite number of near infrared fluorescing molecules that can serve as silent markers, and many of these molecules are visually detectable.

In sum, few practical markers exist, and even fewer practical, silent markers exist. Furthermore, many silent markers are somewhat ill-suited for use in detection systems in that a user must chemically manipulate a sample of the marked product to detect the marker. With the growing drive to prevent brand adulteration of fuel and the widening use of markers around the world for enforcement of taxation, more markers and an improved method of marking are needed.

The invention is next described in connection with certain embodiments; however, it will be clear to those skilled in the art of petroleum product marking that various modifications, additions and subtractions can be made to the described embodiments without departing from the spirit or scope of the invention.

SUMMARY OF THE INVENTION

The present invention is directed to methods for marking a liquid and methods and systems for identifying marked liquids that are easy to use, inexpensive and allow for the creation of a large family of silent markers.

Accordingly, in one aspect of the invention, a liquid can be marked for identification purposes with at least a first marker and a second marker. Each of the markers is miscible with the liquid and each of the markers has an absorbance spectrum with at least one wavelength range where the marker's absorbance is differentiable from the absorbance of the background liquid and any other marker in the liquid. The markers are mixed in the liquid so that the ratio of the concentration of the first marker to the concentration of the second marker is substantially equal to a predetermined value. Thus, when a system according to the invention measures the concentrations of the first and second markers, the system can compare the ratio of the measured concentration of the first marker to the measured concentration of the second marker with a look up table of predetermined values to provide information concerning the identity of the liquid.

Another aspect of the invention provides a method for assisting in the identification of a liquid. The method includes the steps of measuring the concentrations of at least a first marker and a second marker in the liquid and comparing the ratio of the measured concentration of the first marker to the measured concentration of the second marker with a look up table of predetermined values mentioned above so as to assist in the identification of the liquid.

Another version of the invention provides an apparatus for assisting in the identification of a marked liquid. The apparatus includes a vessel for receiving a liquid including at least a first marker and a second marker, a measurement means for measuring the concentrations of at least the first marker and the second marker in the liquid, and a comparison element for comparing the ratio of the measured concentration of the first marker to the measured concentration of the second marker with a look up table of the predetermined value mentioned above so as to assist in the identification of the liquid.

Yet another aspect of the invention essentially provides a quantization solution to the problem of finite markers. This solution provides markers in integral combinations to form marking patterns and couples the markers with a dedicated readout detection system. This version of the invention provides a method for creating families of marking patterns for marking liquids. Significantly, the markers can be common organic chemicals with spectroscopically differentiable signatures, and the readout detection systems can be simple, wavelength specific spectrometers, such as a dedicated wavelength colorimeter. More importantly, the invention provides multiple marking patterns, i.e. a family of marking patterns, from repetitive use of a single set of markers.

A preferred embodiment of the invention utilizes absorbance methods, with the marker chosen for characteristic absorbance in the visible, near infrared or mid infrared spectral regions. Markers with characteristic absorption in the near and mid infrared are specifically useful as silent markers. Although with a quantization approach, even markers with characteristic absorption in the visible spectral region can act as silent markers. In addition, Raman light scattering and chemical assays can be used as the detection method, as well as other spectroscopic approaches, such as fluorescence spectroscopy.

According to one embodiment of the invention, at least one marker is added to a fuel in a specific concentration. Each of the marker chemicals has at least one region where its spectroscopic absorbance is differentiable from the background fuel and, importantly, the other added marker chemicals. The marker chemicals are added in concentrations that are integral multiples of a selected basis concentration. Thus, the identity of a liquid can be encoded in a specific combination of quantized marker concentrations.

For example, a premium brand of gasoline can be marked with marker A, at two times the basis concentration, and with marker B, at three times the basis concentration. While a super premium brand can be marked with marker A, at one times the basis concentration, and with marker B, at one times the basis concentration. When the concentrations of the markers are detected, a particular sample of gasoline can be identified by matching the combination of measured concentrations with one of the unique combinations of marker concentrations used to mark each brand of interest. Thus, if upon measurement of the concentrations of the markers, the fuel is found to have marker A and marker B concentrations equal to two and three times the basis concentration, respectively, the gasoline is identified as premium brand. Conversely, if the fuel is found to have marker A and marker B concentrations of one half and three quarters the basis concentration respectively, the gasoline is identified as not premium brand and perhaps as adulterated gasoline.

The readout device can be an absorbance measurement device tuned to the differentiable absorbance of all the chemicals making up the marking pattern. When a marked sample is introduced into the readout device, the marking pattern is revealed by the characteristic concentration ratios displayed on the readout device, normally in parts per million of each marker component. If the ratios of measured concentrations matches those preset in the marking pattern selected, the product is verified as authentic. Any significant deviation from the expected marking pattern concentration ratios alerts the operator to the potential presence of contaminated or counterfeit fuel.

BRIEF DESCRIPTION OF THE DRAWINGS

These and other features and advantages of the present invention will be more fully understood by reference to the following detailed description in conjunction with the attached drawings in which like reference numerals refer to like elements and in which:

FIGS. 7A, 7B, and 7C show the infrared spectra of fuel containing the marker of FIG. 2 and benzylisocyanate in ratios of 4:1, 2:1 and 8:1, respectively;

DETAILED DESCRIPTION

Figure 1:
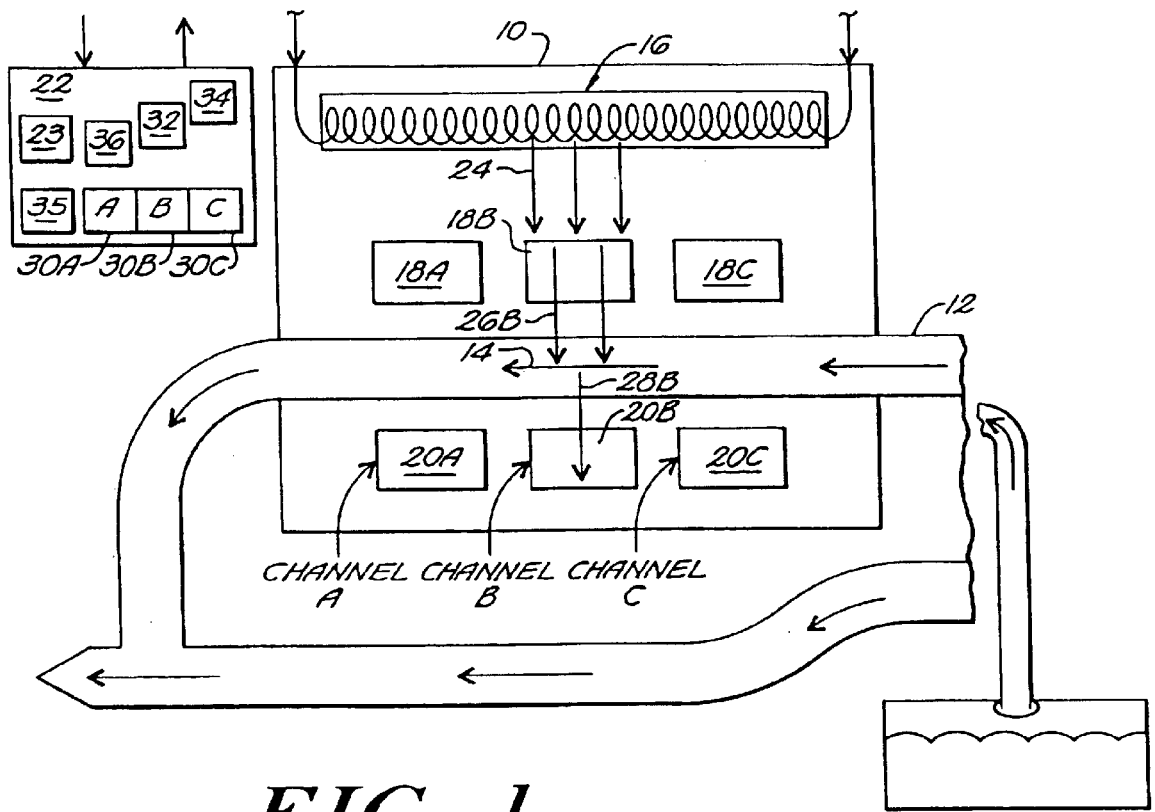
FIG. 1 is a schematic representation of a mid-infrared, multi-channel fuel analyzer according to an embodiment of the invention for detection and quantification of fuel markers.

FIG. 1 is a schematic representation of a multi-channel fuel analyzer according to an embodiment of the invention for detection and quantification of fuel markers contained in fuel flowing through examination vessel or tube 12. Monitor 10 enables evaluation of fuel in-situ. In large capacity operations, a shunt line is tied into the primary fuel line so as to deliver a measurable stream to monitor 10 representative of the larger supply of fuel.

Light source 16, e.g. a heated element acting as a black body radiator, is provided on one side of tube 12 for illuminating the flowing fuel 14. Detectors 20A, 20B, and 20C assigned to channels A, B, and C, respectively, are provided on the other side of the tube for detecting absorption associated with the presence of the assigned fuel marker. Because each detector is assigned to a specific fuel marker of interest, each detector's input is limited to that narrow portion of the electromagnetic spectrum as associated with a selected vibrational mode signature which has been determined to be characteristic of the assigned fuel marker.

Isolation of each detector to an assigned fuel marker is achieved in this embodiment by interposing filters 18A, 18B, and 18C between light source 16 and detectors, 20A, 20B, and 20C, respectively. Each filter passes a narrow band of electromagnetic radiation associated with the signature vibrational mode of the assigned fuel marker. Additional filters and detectors can be employed for detection of yet other markers.

The signal leads for lamp 16 and detectors 20A, 20B, and 20C are connected to a processor and control unit 22 for driving of the lamp, for processing of detection signal from the detectors, and for display of readout information at displays 30A (concentration of a first marker), 30B (concentration of a second marker), and 30C (concentration of a third marker). Displays 32 and 34 are also provided for indication of fuel identity and fuel adulteration.

In operation, as fuel is pumped through tube 12, the light energy 24 from source 16 passes through filters 18A, 18B, and 18C. The filtered radiation 24 covers specific frequency ranges of interest. As shown with respect to channel B, for example, the presence and concentration of a second marker in the fuel is determined when radiation output 26B from filter 18B passes through fuel 14 and detector 20B detects the attenuated beam 28B, representative of the presence and amount of second marker in the fuel. According to Beer's Law, the absorbance due to a marker is directly related to the concentration of the marker in the fuel. Thus, a given detector output is a direct indication of concentration of the detected fuel marker in the tested fuel.

The detector output is received and processed in processor and control unit 22. Processor and control unit 22 includes look up table 23 for storing information about marking patterns, displays 30A, 30B, 30C, 32, and 34 for displaying detection and identification results, comparison element 35 for comparing measured values with values supplied by look up table 23, and receiving element 36 for receiving measured concentration values. As an example, the presence of the second marker and the concentration as volume percent in solution is indicated at display 30B. A receiving element 36 receives signals representative of the measured concentrations of the markers from the processor and control unit 22. The receiving element 36 provides the comparison element 35 with the measured concentrations of the markers. The comparison element 35 can compare the ratio of the measured concentration of the first marker to the measured concentration of the second marker with a predetermined value stored in the look up table 23.

Importantly, a variety of sources, such as visible, mid-infrared, and near-infrared sources, can be used. In addition, the concentration of markers in the liquid can be measured using a fluorescence spectrometer instead of an absorption spectrometer. Furthermore, the concentration of markers in the liquid can be measured using chemical assays or Raman light scattering.

A method, according to one aspect of the invention, for marking a liquid for subsequent identification includes the steps of selecting at least a first marker and a second marker and mixing the markers in the liquid so that the ratio of the concentration of the first marker to the second marker substantially equals a predetermined value. The markers are miscible with the liquid. Furthermore, each of the markers has an absorbance spectrum with at least one wavelength range where the marker's absorbance is differentiable from the absorbance of the background liquid and any other marker in the liquid. Thus measuring the concentrations of the first marker and the second marker, and comparing the ratio of the measured concentration of the first marker to the measured concentration of the second marker with the look up table of the predetermined values assists in identifying the liquid.

Figure 2:
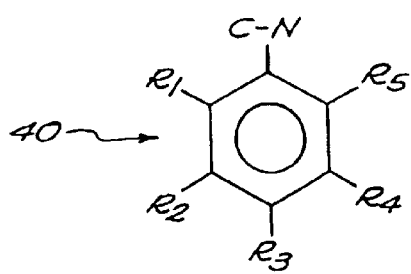
FIG. 2 is an illustration of one type of silent marker for marking a gasoline that can be analyzed with the fuel analyzer of FIG. 1.
Figure 3:
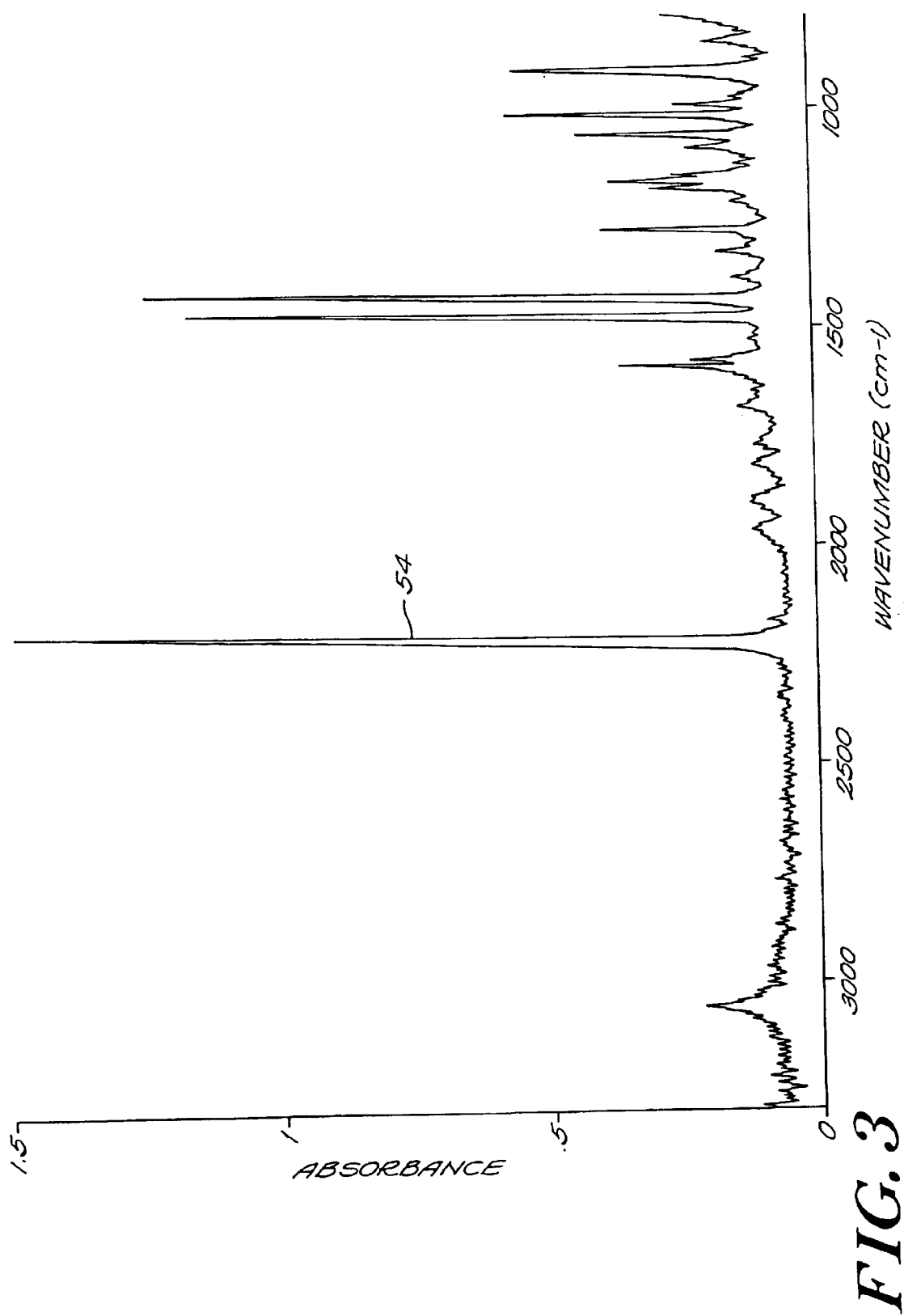
FIG. 3 is the mid infrared spectrum of the marker shown in FIG. 2.
Figure 4:
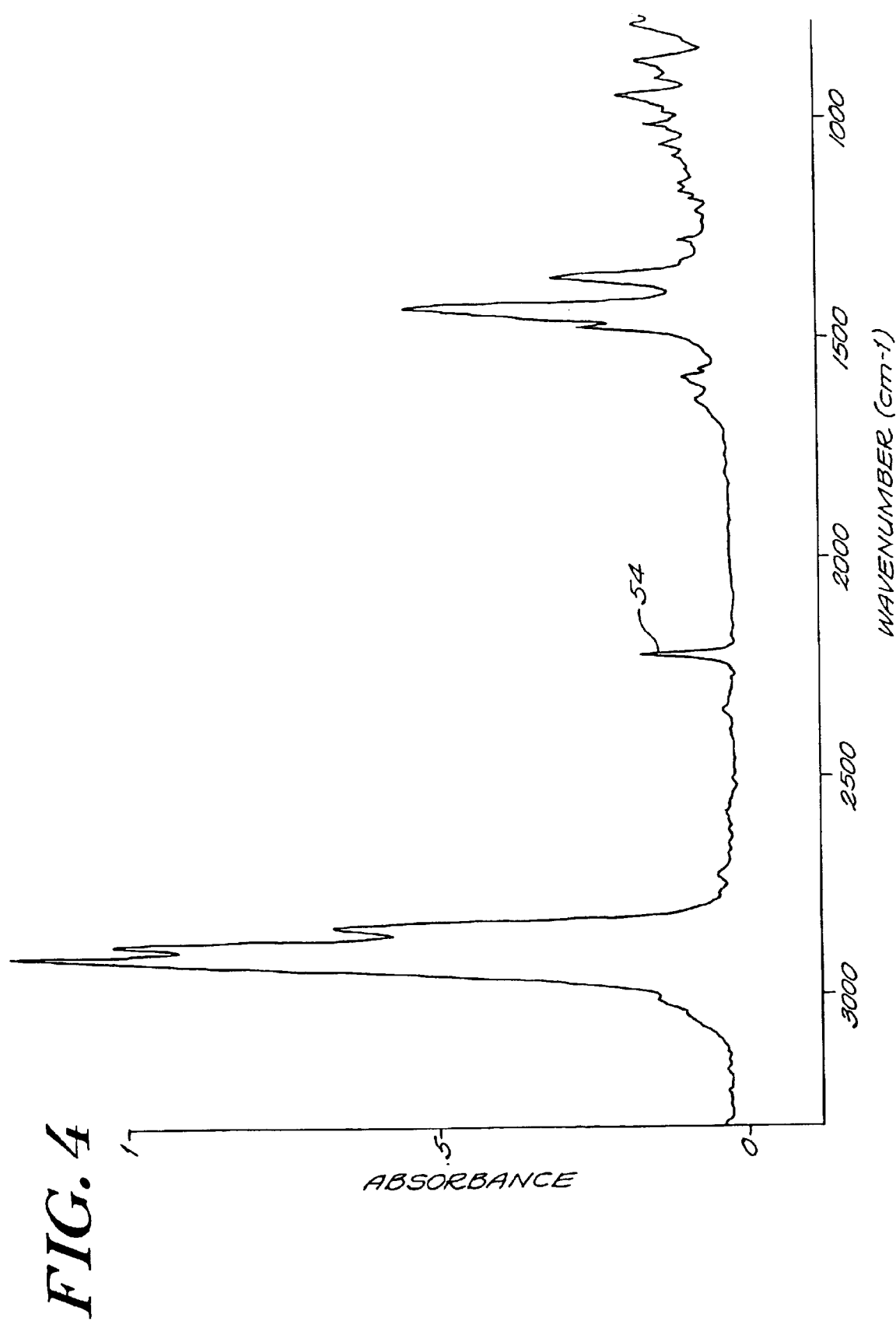
FIG. 4 is the mid infrared spectrum of fuel containing 1% concentration of the marker shown in FIG. 2.

One embodiment of a method, according to the invention, includes adding the common organic solvent cyanobenzene (benzonitrile) to gasoline. FIG. 2 shows cyanobenzene 40. Cyanobenzene is a colorless liquid, highly miscible with hydrocarbons, and can be synthesized both as natural abundance cyanobenzene and as cyanobenzene isotopically enriched with $^{13}$C. The carbon-nitrogen (CN) vibration of the cyanobenzene molecule provides a unique sharp mid infrared absorption band 54 at wavenumber 2230 cm$^{-1}$. The mid infrared spectrum of cyanobenzene is shown in FIG. 3. The mid infrared spectrum of cyanobenzene mixed at about 1% concentration with base gasoline, RFA, is shown in FIG. 4. The components of gasoline do not have significant absorption bands in this region of the electromagnetic spectrum.

Isotopically enriched cyanobenzene will have this same sharp mid infrared feature 56 at the same spectral intensity, slightly displaced to a lower frequency (due to the greater nuclear mass of $C^{13}$ as compared to $C^{12}$), and will appear at approximately 2140 cm$^{-1}$, well resolved from the natural abundance CN band. Thus, one method according to one aspect of the invention, includes adding natural abundance cyanobenzene as a first marker and isotopically enriched cyanobenzene as a second marker.

Other markers that can be used in the present invention include compounds from the class of the phtalocyanine, naphthalocyanine, nickel-dithiolene complexes, aminium compounds of aromatic amines, methine dyes and azulenesquaric acid dyes. These markers fluoresce or absorb at near-infrared wavelengths.

EXAMPLE 1

Figure 5:
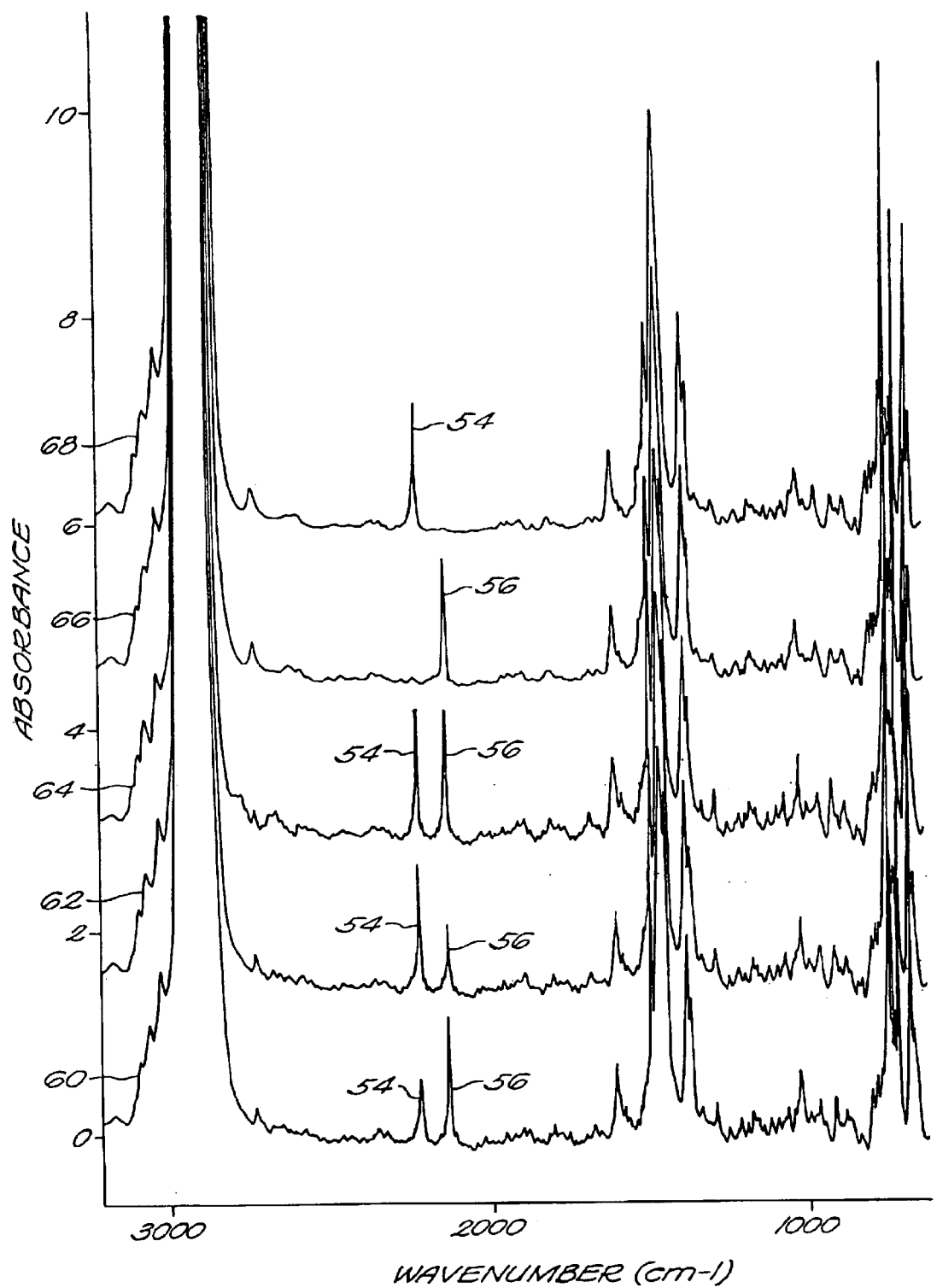
FIG. 5 is a series of mid infrared spectra of fuel containing different combinations of two marker chemicals, one of the marker chemicals being the marker chemical of FIG. 2.
Figure 6:
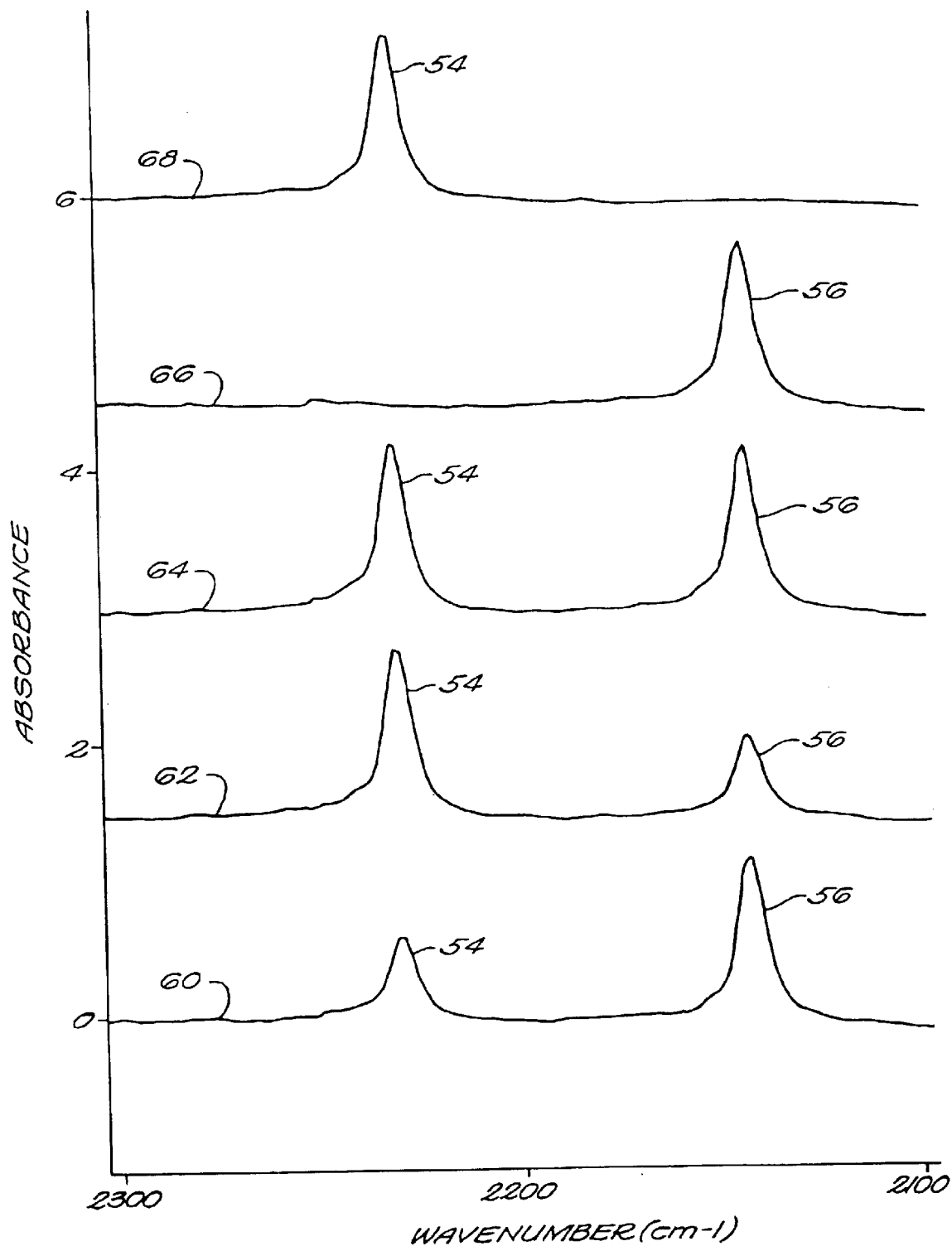
FIG. 6 is a series of mid infrared spectra of fuel containing different combinations of two marker chemicals showing a smaller portion of the spectrum than that shown in FIG. 5.

A series 60, 62, 64, 66, and 68 of mid infrared spectrums of fuel containing different combinations of the two marker chemicals, natural abundance cyanobenzene and isotopically enriched cyanobenzene, are shown in FIGS. 5 and 6. Note that by combining the two marker chemicals in simple concentration ratios, in amounts of 0, 100 and 200 parts per million, this version of the invention defines five unique ways of marking the liquid, i.e. five marking patterns.

These ratios can be expressed by a quantization representation (CN:$^{13}$CN) as 2:0, 0:2, 2:2, 2:1, 1:2. By providing the two above-referenced markers in concentrations corresponding to this quantization representation, FIVE distinct marking patterns are provided from the two marker chemicals. Adding additional multiples of the marker chemicals creates additional marking patterns, all from the same two chemicals.

This illustration provides two key features of the quantization marking pattern approach. First, the specific marker pattern immediately identifies the fuel as authentic by reading out the correct pattern; and second, the measurement of the correct concentrations of the marker chemicals making up the marker pattern establishes that the fuel has not been adulterated. Both features are useful for establishing a successful silent marking system.

EXAMPLE 2

Figure 7C:
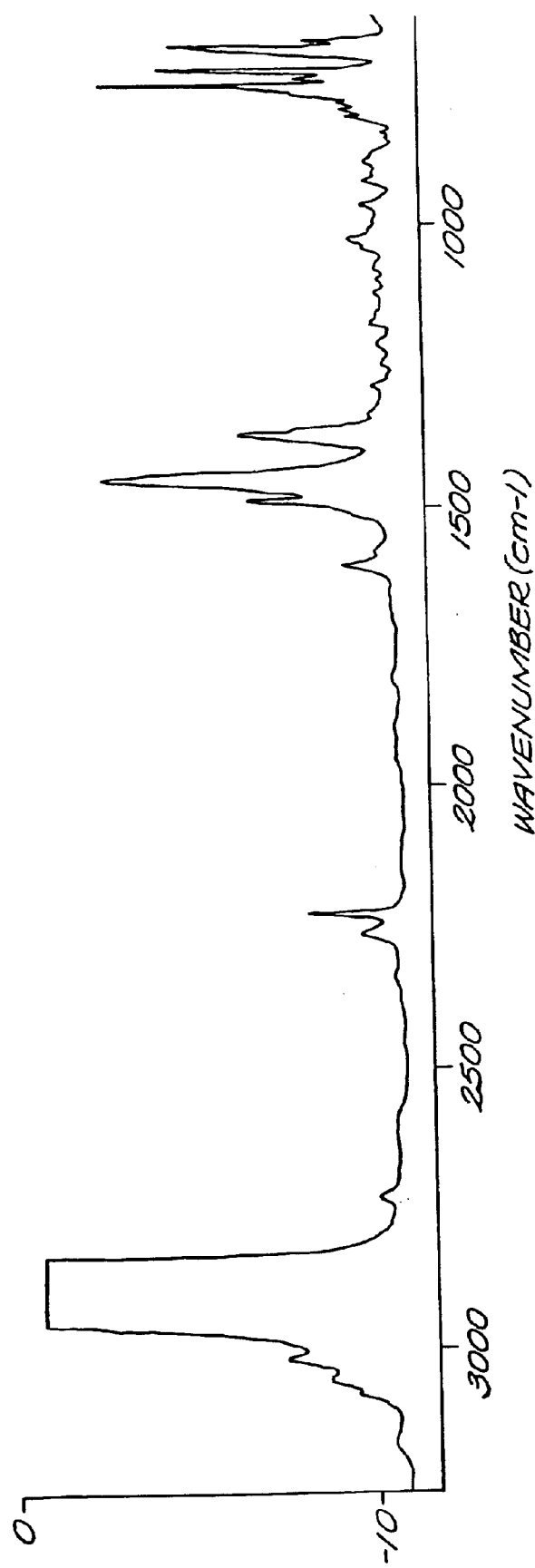

A further example is embodied in a family of marking patterns for gasoline made up by adding the two distinct chemicals, cyanobenzene and benzylisocyanate to fuel. Both are miscible in gasoline and other hydrocarbon fuels. Both chemicals have strong, sharp, distinguishable absorbance bands in the mid-infrared at wavenumbers 2230 and 2268 cm$^{-1}$, respectively, but with absorbance strength at these frequencies in the approximate ratio of 1:4, also respectively. Further, these two bands are distinct from the background fuel absorbance of gasoline, which contains no chemical components with CN substituents in any of its blendants. The infrared spectra of fuel containing different combinations of the two marker agents (at about 1% concentration) are shown in FIGS. 7A, 7B, and 7C. In FIG. 7A cyanobenzene and benzyl isocyanate have a ratio of concentration of approximately 4:1, respectively. FIGS. 7B and 7C show ratios of concentration of approximately 2:1 and 8:1, respectively.

Figure 8:
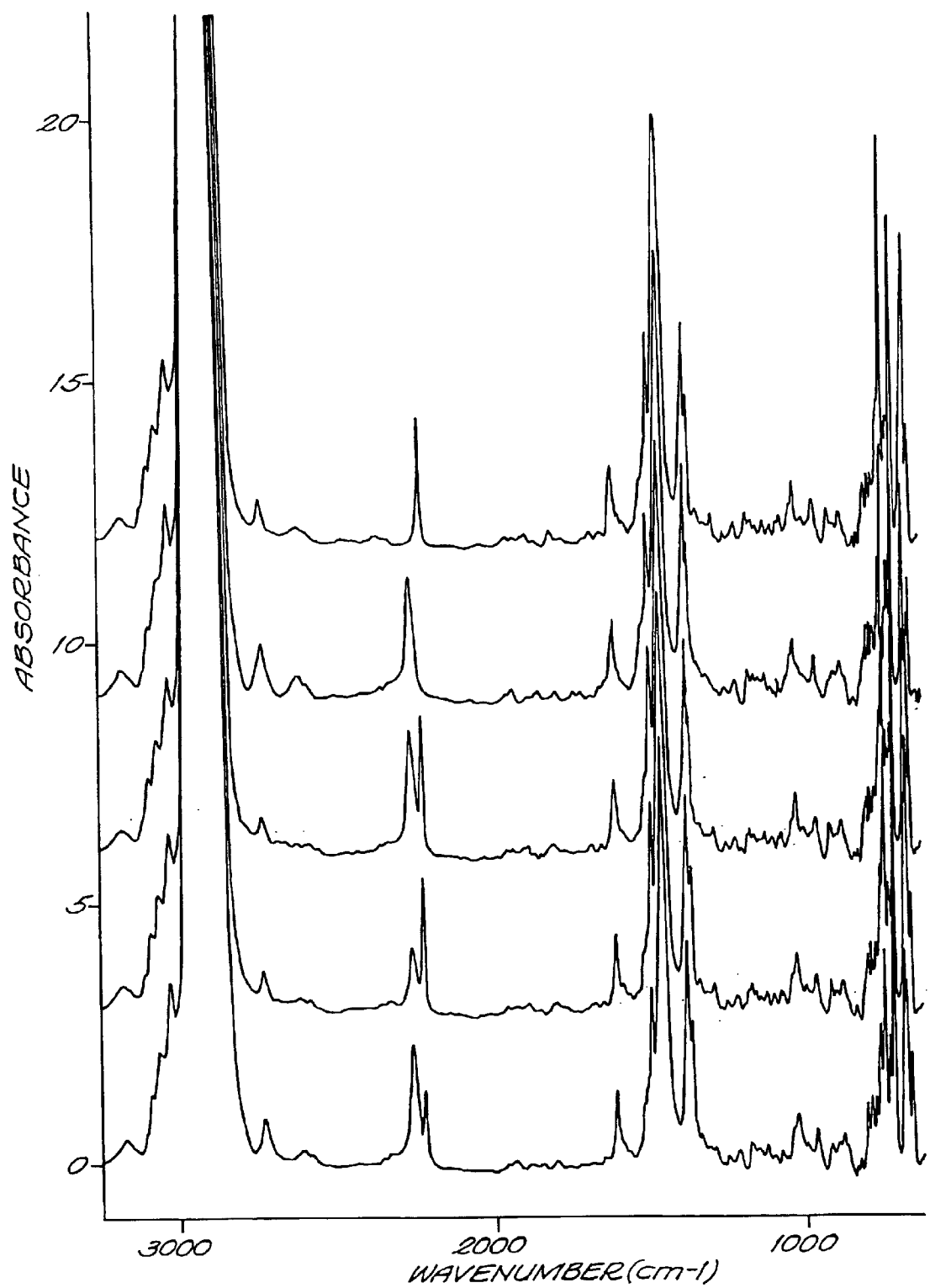
FIG. 8 is a series of mid infrared spectra of fuel containing different combinations of two marker chemicals, one of the marker chemicals being the marker chemical of FIG. 2 and the other being benzylisocyanate.
Figure 9:
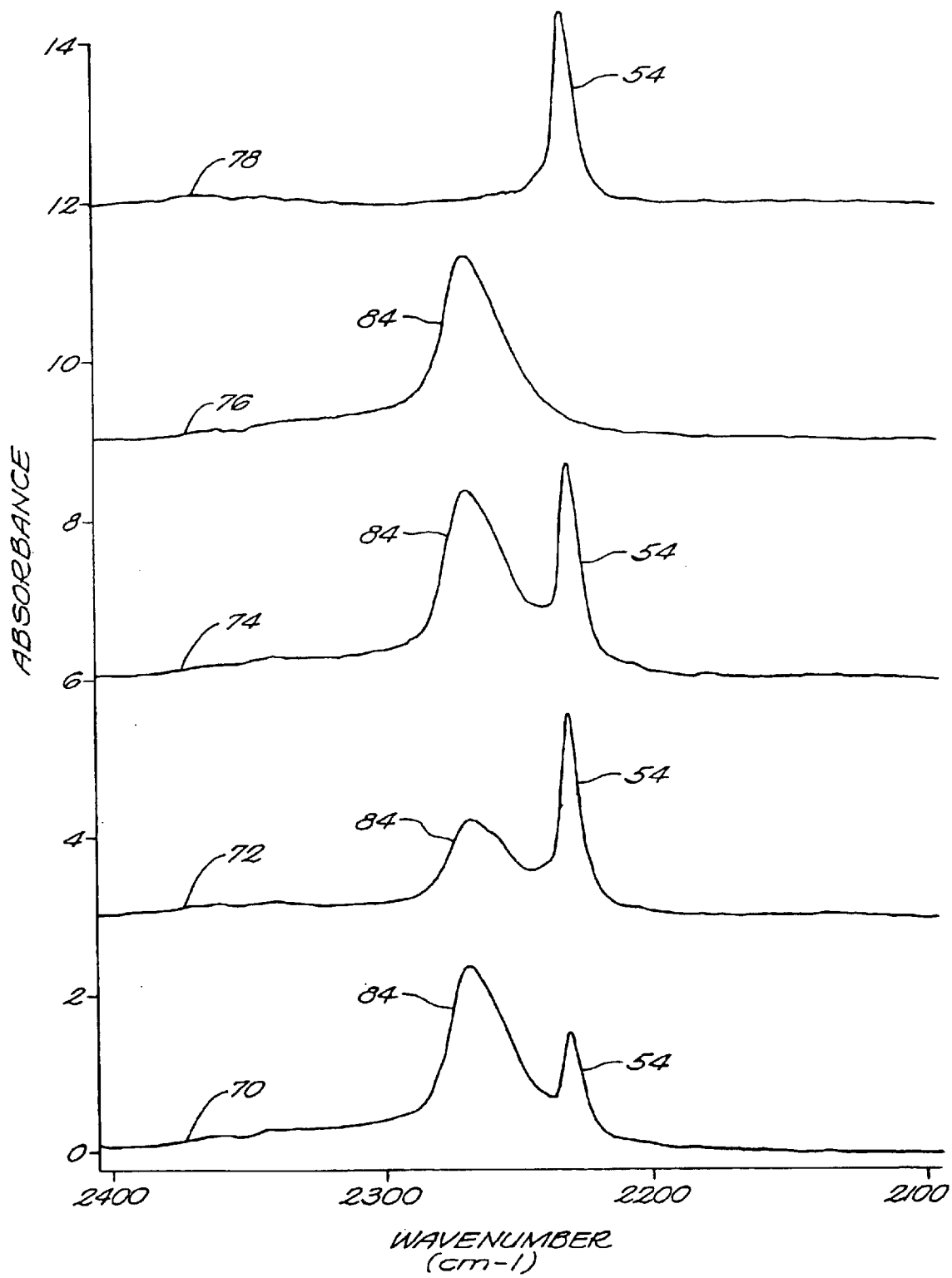
FIG. 9 is a series of mid infrared spectra of fuel containing different combinations of two marker chemicals showing a smaller portion of the spectrum than that shown in FIG. 8.

A whole family of marking patterns for gasoline is made up from these two marker chemicals as follows. One marker consists of 200 ppm cyanobenzene and 100 ppm benzylisocyanate, resulting in approximately a 1:2 pattern; a second consists of 200 parts-per-million (ppm) cyanobenzene and 25 ppm benzylisocyanate, producing a roughly 2:1 peak intensity ratio; a third has equal intensities of both marker chemicals; a fourth has no cyanobenzene and 100 ppm benzylisocyanate; a fifth has 200 ppm cyanobenzene and no benzylisocyanate. These marking patterns are shown in FIGS. 8 and 9. A series 70, 72, 74, 76, and 78 of mid infrared spectrums of fuel containing different combinations of the two marker chemicals, natural abundance cyanobenzene and benzylisocyanate, are shown in FIGS. 8 and 9. FIG. 9 shows a smaller portion of the spectrum than that shown in FIG. 8. The characteristic band 54 of cyanobenzene is distinct from the characteristic band 84 of benzylisocyanate.

Note that the ratios do not have to be exact, only the pattern has to be clearly discernible. A simple readout detector system can directly readout the marker concentrations. Such a system consists of an infrared source and filters set to measure the sample absorbance at 2230 and 2268 cm$^{-1}$. One such system is a version of a PetroSpec GS-1000 filter-based infrared gasoline analyzer, available from Boston Advanced Technologies, Inc., located in Marlborough Mass., and described in U.S. Pat. No. 5,225,679, incorporated herein by reference. The PetroSpec GS-1000 analyzer can measure chemical components of fuels. The GS-1000 analyzer can function as a readout device with optical filters appropriate for the marker chemicals used and with a cell path length appropriate for the range of concentrations of marker chemicals selected.

Use of this readout system on site would provide the user an instant verification of the nature of the fuel sample as the marker concentrations and their ratios are displayed. The number of marking patterns defined by two marker chemicals is limited only by measurement sensitivity and capability of the readout system. Additional integral combinations of concentrations of two marker chemicals include 2:2, 3:1, 1:3, 3:2, 2:3, 3:3. Note that the actual concentrations used can be adjusted to provide for ease of readout detection depending on the fuel marked and are not limited to the concentration ranges in the examples given.

Again, as in the previous example, any significant deviation from the concentration ratio indicates counterfeit fuel. Additionally, any significant deviation from the preset concentration values of either marker chemical indicates adulteration of the fuel. Thus, markers protect the integrity of a fuel source by indicating counterfeiting and adulteration. The magnitude of a deviation that is considered significant depends on the resolution of the concentration measurement system and the accuracy with which the concentrations of markers is determined at the time of marking the liquid.

Extension to a three chemical marking pattern provides even more marking patterns on the basis of the quantization marker approach. Adding a third chemical similar to the above examples of cyanobenzene and benzylisocyanate, such as an isothiocyanate or benzylcyanate isomers, provides a slightly shifted signature infrared band in the 2000 $cm^{-1}$ region, and the possibility of a large number of marking patterns. In quantization form such combinations (cyanobenzene/benzylisocyanate/isomer, represented as XYZ) as 100, 010, 001, 110, 101, 011, 111, 210, 021, 012, 211, 121, 112, 221 and other combinations in continuing progression provides a huge inventory of marking patterns, all originating from only three distinct chemicals.

In all the above embodiments of the invention, the marker chemicals have no visible absorbance (no color) and are, therefore, undetectable by visual inspection. This feature makes them ideal candidates for a family of silent markers. Even if visual dyes are added for other purposes, the silent marker nature of the above example is still intact, as long as the added visual dye does not coincidentally have an infrared feature at 2230, 2268 $cm^{-1}$, or any of the other infrared bands utilized in reading out the marking pattern.

Figure 10:
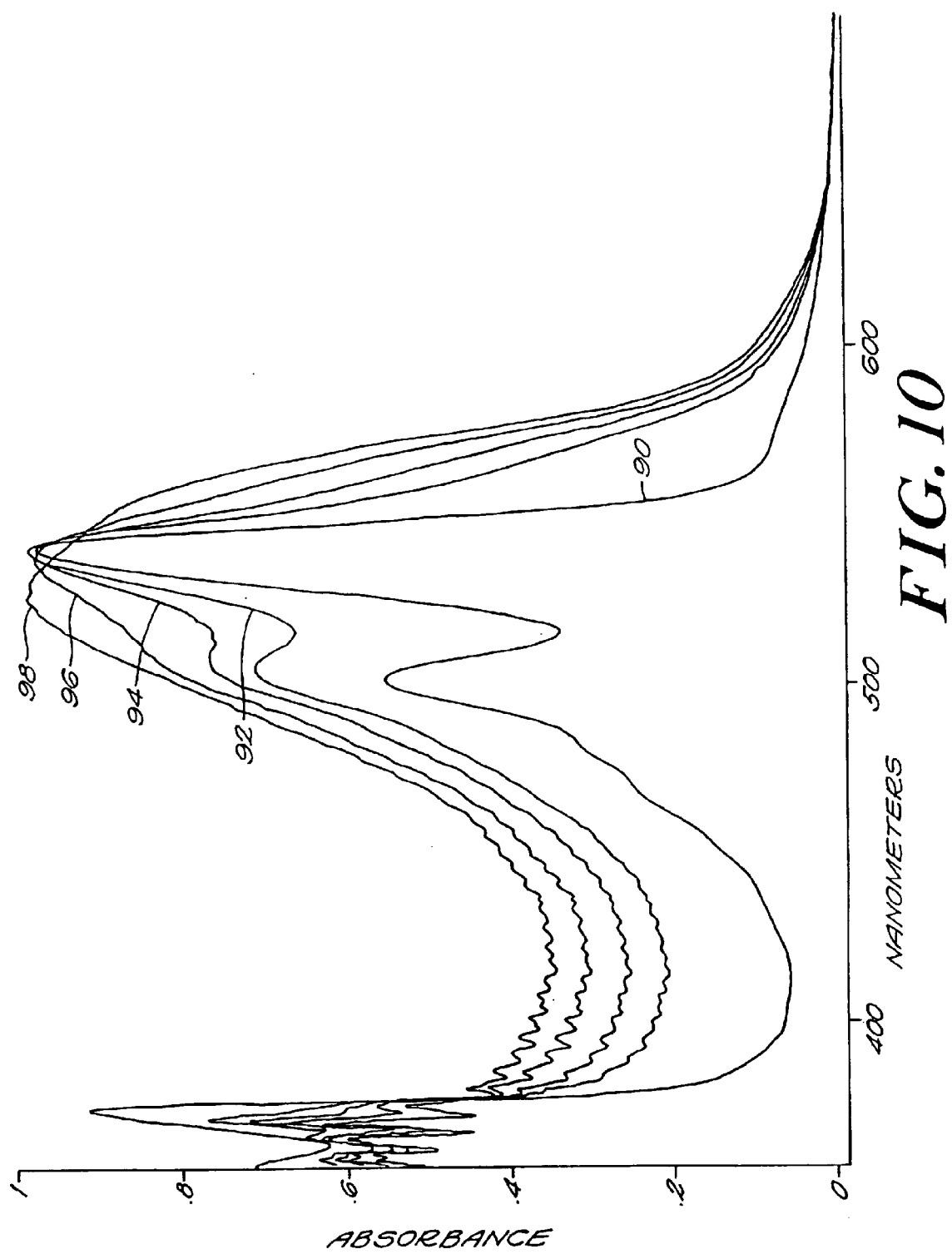
FIG. 10 is a series of visible spectra of fuel containing Red-26 and FY131SC dyes in different combinations as measured by a device based on the principles of the device shown in FIG. 1.

Yet another version of the invention can provide silent marker capability even with visual dyes. A unique feature of the invention's quantization approach means that the marker can be coded into a system which is visible to an observer. In an embodiment of the invention in which two dyes are added to a fuel sample that impart color in the same region of the visible spectrum, a combination of the dyes may be added to form a marking pattern that is not evident from the color. FIG. 10 shows the absorbance spectrum of two dyes, Morton Red-164 and FY131SC. FY131 SC alone is shown by spectrum 90. Red-164 alone is shown in spectrum 98. Spectra 92, 94, and 96 show Red-164 and FY131SC in concentration ratios of 1:1, 2:1, and 5:1, respectively. Both dyes impart a red coloration to fuel. When the two dyes are present together, the fuel still appears red, irrespective of the concentrations—or ratio of the concentrations—of either dye present.

EXAMPLE 3

The two dyes may constitute a family of markers in the following manner. FIG. 10 shows a series of mixtures of Morton 164 (Red-26) and FY131SC in varying parts-per-million concentration ratios from 5:1 to 1:1. All the mixtures appear red to an observer, since an observer cannot differentiate from which dye the color originates. But a simple readout device set to measure the absorbance at a wavelength specific to each marker dye, 520 nm for Red-26 and 550 nm for 131SC, can readily determine the amount of each dye present. A family of silent markers is quickly established on this basis, 5:1, 1:1, 1:5, for example. Each combination is a separate marking pattern and any deviation from the preset ratio and concentration indicates unauthorized or adulterated fuel.

Using a PetroSpec DT-100 portable dye analyzer, available from Boston Advanced Technologies, Inc., located in Marlborough Mass., set for the above wavelengths and calibrated for the two dyes mixed simultaneously in a gasoline sample, the approach according to the invention was tested on the red dye system. The filters of the DT-100 analyzer were set for the Red-26 and Y131-SC dyes and calibrated for a range of combinations of the two dyes. All samples appeared to be equally red colored to an observer. The DT-100 analyzer measured a series of samples with concentrations made up to a consistent red coloration, and the data obtained is as follows:

|  | Actual | | Instrument reading | |
| --- | --- | --- | --- | --- |
|  | FY131SC (ppm, v/v) | Red 26 (mg/L) | FY131SC (ppm, v/v) | Red 26 (mg/L) |
| Test Solution #1 | 0 | 0.0 | 0 | 0.0 |
| Test Solution #2 | 0 | 2.0 | 0 | 1.8 |
| Test Solution #3 | 50 | 0.0 | 47 | 0.0 |
| Test Solution #4 | 50 | 2.0 | 49 | 1.9 |

The results indicate that a visible readout device set up to operate on the principle of the DT-100 analyzer is capable of providing a system for silent markers in the visible range of the spectrum.

This approach according to the invention can be generalized to other combinations of dye agents to create a marker family of silent markers using a DT-100 analyzer or equivalent device.

In sum, the present invention benefits from the recognition that a fuel can be simply and relatively inexpensively marked and subsequently identified by using distinct markers to create quantized marling patterns. It will be understood that the above description pertains to only several embodiments of the present invention. That is, the description is provided by way of illustration and not by way of limitation. The invention is further characterized according to the following claims.

What is claimed is:

1. An apparatus for assisting in the identification of a marked liquid, the liquid comprising a plurality of markers miscible with the liquid and present in a predetermined pattern of relative concentrations, the apparatus comprising:
   a detector for detecting the plurality of markers and for generating signals indicative of relative concentrations of each of the markers, the signals defining a measured concentration ratio; and
   a data processor connected to the detector comprising:
      a receiver to receive the signals from the detector and determine therefrom a measured concentration ratio of the markers;
      a look-up table storing a plurality of known concentration ratios, each concentration ratio corresponding to the signal from a specific combination of the plurality of markers at predefined relative concentrations; and
      a ratio comparison element capable of comparing the measured concentration ratio with known concentration ratios of identified liquids, the known ratios being accessible, via the look up table, to the ratio comparison element, so as to permit the identification of the marked liquid.

2. The apparatus of claim 1, wherein said detector is a spectroscopic detector.

3. The apparatus of claim 1, wherein said spectroscopic detector is an absorption spectrometer.

4. The apparatus of claim 3, wherein said absorption spectrometer is a near infrared spectrometer.

5. The apparatus of claim 3, wherein said absorption spectrometer is a mid-infrared spectrometer.

6. The apparatus of claim 3, wherein said absorption spectrometer operates in the visible spectrum.

7. The apparatus of claim 2, wherein said spectroscopic detector is a fluorescence spectrometer.

8. The apparatus of claim 7, wherein said fluorescence spectrometer is a near infrared spectrometer.

9. The apparatus of claim 2, wherein said spectroscopic detector is a calorimeter.

10. The apparatus of claim 2, wherein said spectroscopic detector is a Raman spectrometer.

11. The apparatus of claim 1, wherein said detector is limited to those portions of the electromagnetic spectrum associated with select vibrational mode signatures characteristic of said plurality of markers.

12. The apparatus of claim 1, further comprising at least one additional detector, wherein the detector is limited to that portion of the electromagnetic spectrum associated with a select vibrational mode signature characteristic of a first marker and wherein the at least one additional detector is limited to that portion of the electromagnetic spectrum associated with a select vibrational mode signature characteristic of another of the plurality of markers.

13. The apparatus of claim 12, wherein the detector measures a nitrile vibration and the at least one additional detector measures an isotopically labeled carbon-nitrile vibration.

14. The apparatus of claim 12, wherein the detector measures infrared absorption band of a nitrile vibration at 2230 $cm^{-1}$ and the at least one additional detector measures an isotopically labeled carbon-nitrile infrared absorption band at $2140^{-1}$ cm.

15. The apparatus of claim 12, wherein the detector measures a nitrile vibration and the at least one additional detector measures an isocyanate vibration.

16. The apparatus of claim 12, wherein the detector measures infrared absorption band of a nitrile vibration at 2230 $cm^{-1}$ and the at least one additional detector measures an isocyanate infrared absorption band at $2268^{-1}$ cm.

17. The apparatus of claim 12, wherein the detector measures absorbance at a wavelength of 520 nm and the at least one additional detector measures absorbance at a wavelength of 550 nm.

18. The apparatus of claim 1 wherein said comparison element is a dedicated mucroprocessor.

19. The apparatus of claim 12, wherein said comparison element is a dedicated microprocessor.

20. A system for assisting in the identification of a marked liquid, comprising:
   a plurality of silent markers miscible with a liquid to be identified; and
   a detector for detecting the plurality of silent markers and for generating signals indicative of relative concentrations of each of the silent markers; and
   a data processor connected to the detector comprising:
      a receiver to receive the signals from the detector and determine therefrom a measured concentration ratio of the markers;
      a look-up table storing a plurality of known concentration ratios, each concentration ratio corresponding to the signal from a specific combination of the plurality of silent markers at predefined relative concentrations; and
      a ratio comparison element capable of comparing the measured concentration ratio with known concentration ratios of identified liquids, the known ratios being accessible, via the look up table, to the ratio comparison element, so as to permit the identification of the marked liquid.

21. The system of claim 20, wherein said detector is limited to those portions of the electromagnetic spectrum associated with select vibrational mode signatures characteristic of said plurality of markers.

22. The system of claim 20, further comprising at least one additional detector, wherein the detector is limited to that portion of the electromagnetic spectrum associated with a select vibrational mode signature characteristic of a first marker and wherein the at least one additional detector is limited to that portion of the electromagnetic spectrum associated with a select vibrational mode signature characteristic of another of the plurality of markers.

23. The system of claim 22, wherein the detector measures infrared absorption band of a nitrile vibration at 2230 $cm^{-1}$ and the at least one additional detector measures an isocyanate infrared absorption band at $2268^{-1}$ cm.

24. The system of claim 22, wherein the detector measures absorbance at a wavelength of 520 nm and the at least one additional detector measures absorbance at a wavelength of 550 nm.

* * * * *